Figure 1:
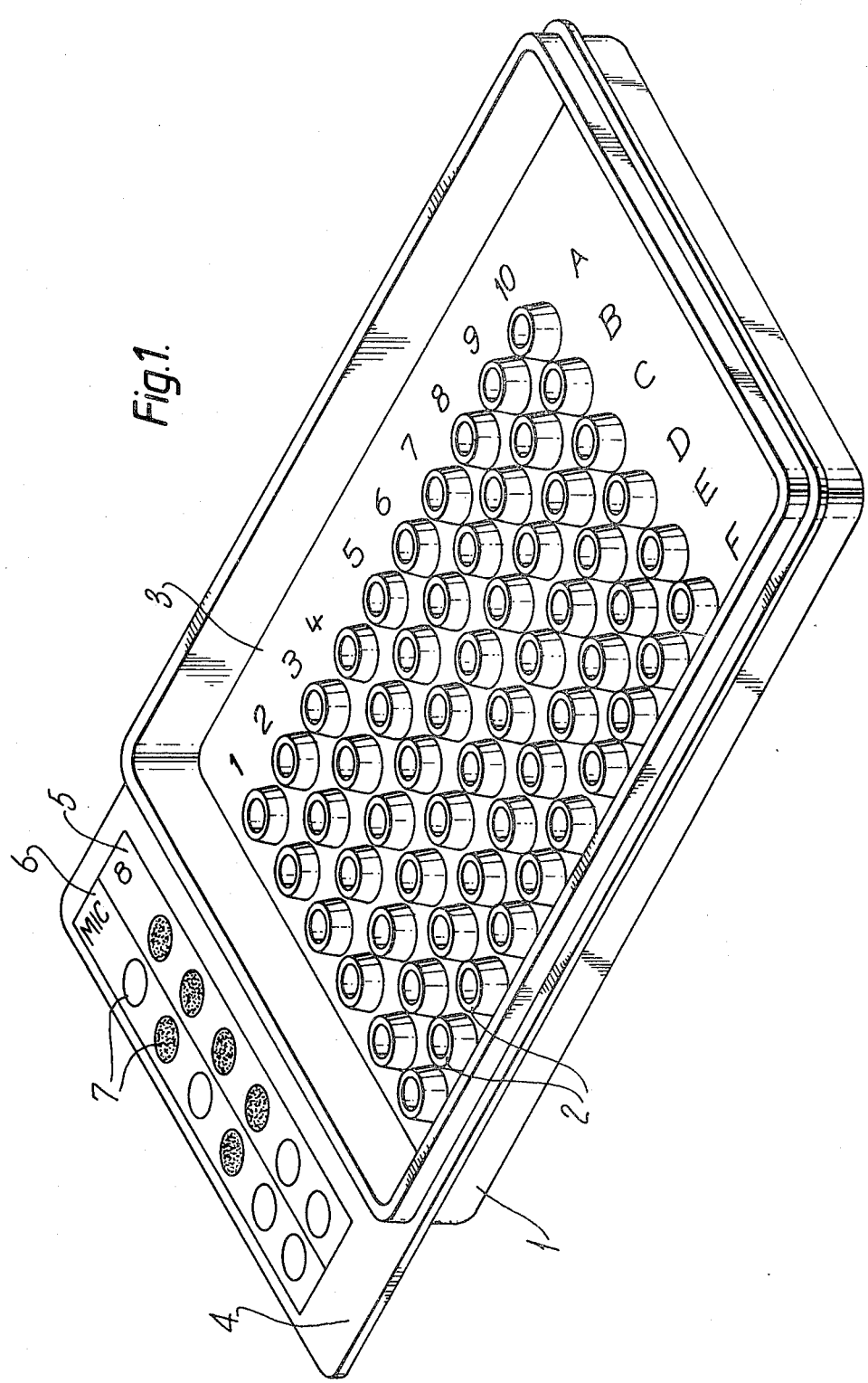

United States Patent [19]

Suovaniemi

[11] 4,431,307
[45] Feb. 14, 1984

[54] SET OF CUVETTES

[75] Inventor: Osmo A. Suovaniemi, Helsinki, Finland

[73] Assignee: Labsystems Oy, Finland

[21] Appl. No.: 323,108

[22] Filed: Nov. 19, 1981

[51] Int. Cl.³ .............................................. G01N 1/10
[52] U.S. Cl. .................................... 356/246; 356/440; 422/73; 422/102; 435/808
[58] Field of Search ................. 356/244, 246, 440; 250/526; 422/73, 102; 435/291, 808, 809

[56] References Cited

U.S. PATENT DOCUMENTS

| 3,873,217 | 3/1975 | Anderson et al. | 356/246 |
| 3,883,308 | 5/1975 | Matte | 356/246 X |
| 4,314,970 | 2/1982 | Stein et al. | 356/246 X |

Primary Examiner—William L. Sikes
Assistant Examiner—Matthew W. Koren
Attorney, Agent, or Firm—Hopgood, Calimafde, Kalil, Blaustein & Judlowe

[57] ABSTRACT

A set of cuvettes the side walls of whose cuvettes (2) are provided with a layer (29) of material that prevents measurement radiation and/or light (22) directed at the walls from passing through the side walls. The layer (29) inhibiting the passage of the measurement radiation may be placed on the inside face and/or on the outside face of the side walls of the cuvettes (2). When the inside face of the measurement window (16) in the cuvettes (2) is coated with a thin layer (34) of the material contained in the side walls of the cuvettes and preventing the passage of radiation, the layer of coating on the measurement window is, however, so thin that it allows the passage of the major part of the radiation through the window.

1 Claim, 4 Drawing Figures

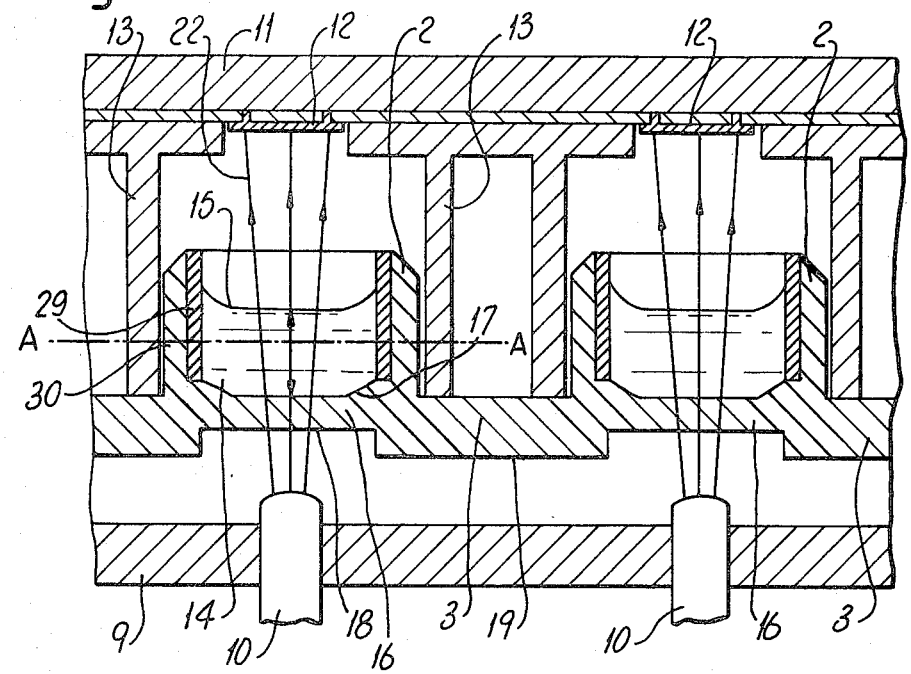
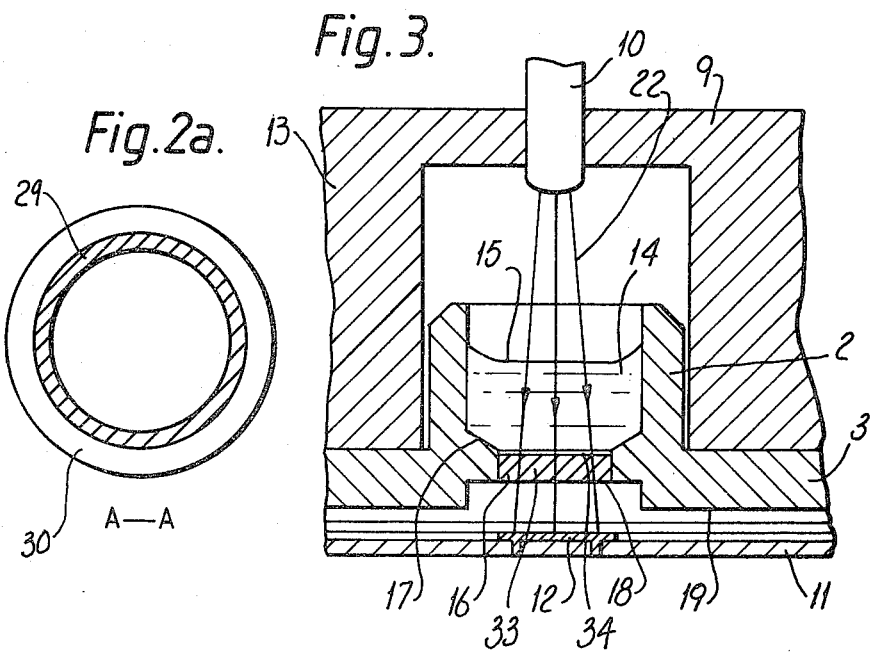

SET OF CUVETTES

The present invention is concerned with a set of cuvettes which comprises several cuvettes and which is intended for use in a photometer of the type of vertical measurement, each cuvette being provided with a bottom window for optical reading. With the exception of the optical windows in the bottom parts of the cuvettes, the parts of the cuvette set are impervious to the light of measurement.

Thus, a set of cuvettes consisting of several cuvettes is concerned wherein the cuvettes are connected to each other permanently or detachably and which is intended to be used for the measurement of the properties of a reaction mixture contained in the cuvettes by means of radiation and of a detector that receives radiation, whereat the beam of measurement passes substantially in the direction of the vertical axis of the cuvette through the measurement window in the bottom of the cuvette.

Cuvette sets made of a transparent material involve the problem that, during measurement, the beams of measurement passing via different cuvettes must be separated from each other by means of walls placed between the cuvettes, for in the contrary case the diffused light from parallel beams of measurement and from the environment disturbs the measurement of adjoining cuvettes.

The set of cuvettes in accordance with the present invention is characterized in that the side walls of the cuvettes are provided with a layer of material that prevents measurement radiation and/or light directed at the walls from passing through the side walls.

The vertical wall of each cuvette in the cuvette-set matrix is either partly or wholly of a material impervious to the beams of measurement and/or partly or wholly of a material different from the material of the optical window of each cuvette, wholly or partly pervious to the beams of measurement. Alternatively, the material of the entire cuvette-set matrix may be different, e.g., of different colour, different material, and impervious to the beams of measurement, as compared with the optical window of each cuvette in the cuvette-set matrix. In such a case the optical window of each cuvette in the cuvette-set matrix is usually well pervious to the beams of measurement and transparent. One requirement imposed on the optical windows of a cuvette-set matrix is that they are transparent, for which reason they must be extruded out of transparent material, such as polystyrene, acrylic plastic, PVC, or TPX. As the cuvette-set matrix can be extruded out of two different materials, it is possible to take into account that the optical window of each cuvette in the cuvette-set matrix is pervious to the beams of measurement and the rest of the matrix either wholly or partly of a different type (physically and/or chemically) in consideration of inhibition of the transfer of the beams of measurement from one cuvette to the other and of the binding of a reagent of the desired type to the plastic material.

In a preferred embodiment of the invention the optical windows of the cuvettes are placed higher than the level of the bottom face of the cuvette-set matrix, being protected, e.g., from dirt and scratches, and in each cuvette the upper face of the optical window corresponds the curve form of the liquid surface in the cuvette so that the path of light in the liquid is equally long as if the upper face of the optical window in each cuvette and the free surface of the liquid in the cuvette were horizontal. Moreover, at some edge of the cuvette-set matrix in accordance with the present invention there may be an optically readable code in which one part informs the measurement apparatus as to what method is concerned and the other part states what number or letter constitutes the code of the cuvette-set matrix concerned.

The cuvette-set matrix in accordance with the invention is suitable for use in analyzer apparatuses operating by means of the principle of vertical measurement (Suovaniemi, Osmo: "Performance and Properties of the Finnpipette Analyzer System", *Proceedings of the Second National Meeting on Biophysics and Biotechnology in Finland,* 183, 1976, and "Method for the improvement of the dosage and measurement results of chemical analyses", U.S. Pat. No. 4,144,030) such as FP-9 and FP-901 Analyzer Systems (Labsystems Oy, Finland) as well as Titertek Multiscan (Eflab Oy, Finland).

In a cuvette-set matrix the reaction results and codes can be measured in one wide matrix so that the measurement radiation or any other measurable signal, produced for each sample and code, is passed to each cuvette and code of the matrix and further to the corresponding detector in the vertical direction.

The cuvette-set matrix to be described now is suitable for methods in which measurements based, e.g., on photometry, spectrophotometry, fluorometry, turbidometry, or on the use of laser beam are used.

The cuvette-set matrix is highly suitable, e.g., in EIA (enzyme immuno assay) reactions, blood-group serology (e.g. ABO and Rh), in HLA (human leucocyte antigen) serology, in MIC (minimum inhibitory concentration) determinations, like also in other types of ascertaining of the growth or inhibition of growth of microorganisms, and further in all methods based on the CF (complement fixation) phenomenon.

The following list includes some of the advantages of the cuvette-set matrix in accordance with the present invention:

1. Each cuvette in the cuvette-set matrix prevents the beams of measurement of the cuvette from disturbing the measurement of the adjoining cuvettes, because only the optical windows are pervious to the beams of measurement.

2. The choice of the raw-material for the cuvette-set matrix is very free in the other respects except regarding the optical windows. When the cuvette-set matrix is extruded out of two different materials, for the optical windows it is possible to select a raw-material well pervious to the beams of measurement and, for the other parts, either wholly or partly, a raw-material that is poorly pervious to the beams of measurement and to which some desired reagent (e.g., antigen, antibody, enzyme) can be possibly fixed easily and in the desired way.

3. In the optical window of each cuvette in the cuvette-set matrix, the portion of the window facing towards the inside of the cuvette may also be of a different material, and preferably of the same material as the other parts of the cuvette-set matrix. In such a case the inside portion of the optical window well pervious to the beams of measurement may be a thin layer of a material which can bind certain reagents in the desired way and which can, in certain cases, function as the optical window alone. This thin layer, constituting a part of the optical window, made of a material different from the material of the optical window, and placed on the inside of the cuvette, inhibits the passage of the beams of measurement the less, the thinner it is.

This construction makes it possible that the inside face of each cuvette in the cuvette-set matrix is of the same material and, consequently, has the same and the desired chemical and/or physical ability to bind reagents. Thereby the area having a certain binding ability in each cuvette is also enlarged, and, as a consequence of that, the sensitivity and reliability of the analysis method at each particular time in use is improved.

4. When the optical windows of the cuvette-set matrix are of a material different from the rest of the cuvette, either wholly or partly, the inside of each cuvette can be coated with some third material, either at the production stage or later. This material used for the coating may act so that it forms a bond of a desired kind with the reagent.

5. The method in accordance with the present invention can also be applied to a cuvette-set matrix that consists of a separate support of individual cuvettes and of cuvettes placed onto this support so as to constitute a matrix, which cuvettes may, in the way described above, be made of two different raw-materials. The transfer of beams of measurement from one cuvette into the other and, that way or in any other way, disturbance of the measurement taking place in the adjoining cuvettes may be prevented by manufacturing the support of the cuvettes and/or the cuvettes themselves out of a material impervious to the beams of measurement.

The invention will be described in more detail below with reference to the attached drawings, wherein FIG. 1 is a perspective view of a cuvette-set matrix in accordance with the invention, FIG. 2 shows a vertical section of a part of the cuvette-set matrix, FIG. 2a shows a section at a—a in FIG. 2, and FIG. 3 shows a vertical section of one cuvette of the cuvette-set matrix.

In FIG. 1 the cuvette-set matrix 1 includes cuvettes 2, a matrix base 3, a code position 4, and therein a number code 5 and a method code 6, both of which can be read by using the same type of a beam of measurement for each element 7 of the code as is used for each cuvette 2.

In FIG. 1 each cuvette in the cuvette-set matrix is coded by means of number 1 to 10 (vertical line) and by means of letter A to F (horizontal line). Thereby the apparatus of measurement indicates the results in the order, e.g., as follows:

*MIC* 8 *A* 1 0.050
8 *A* 2 0.125 which means that in the MIC method, in the 8th cuvette-set matrix, e.g., the absorbance value of cuvette A 2 is 0.125. The results may of course also be indicated as values other than absorbance values, and, moreover, they may be classified and/or combined in the way most appropriate in each particular case, e.g. by making use of the electronics of the apparatus of measurement in consideration of the requirements of the method at each particular time concerned, or of any other requirements.

FIG. 2 shows two cuvettes 2 of the cuvette-set matrix as a sectional view and as placed in the measurement head of the measurement apparatus. In FIG. 2 the matrix 9 of measurement beams and therein the sources 10 of measurement beams are seen below each cuvette 2. Above the cuvettes there are the detector matrix 11 and therein the detectors 12. For each cuvette 2 there are the corresponding sources 10 of measurement beams and detectors 12. In FIG. 2 each cuvette 2 is protected from measurement beams of the adjoining cuvettes, from diffused beams, external beams, and from any other radiation disturbing the measurement by means of a limiter 13 placed around the cuvettes.

In FIG. 2, the cuvette 2 is illustrated as containing liquid 14, whose free liquid surface 15 is concave. In order to compensate for this concavity, the inside face of the window 16 of each cuvette 2 is provided with an additional rim or equivalent appendix 17, by means of which, despite the curved form of the liquid surface 15, the path a of light in the liquid is maintained as long as possible. The length of the path a of light and the height of the liquid column are substantially equal at every point of the cuvette, also at the sides. In FIG. 2, the lower face 18 of the optical window 16 is placed higher than the bottom face 19 of the cuvette-set matrix.

In FIG. 2, the inner face of the cuvettes 2 in the cuvette-set matrix is protected by a protective layer 29, which prevents the entrance of radiation disturbing the measurement into the cuvette. In the section a—a of FIG. 2, in FIG. 2a, the protective layer 29 and a wall portion 30 are seen. The operation of the protective layer 29 shown in FIG. 2 substitutes for limiters 13 and, moreover, it may be made of the material appropriate in each particular case for binding the desired reagent (e.g. antigen, antibody, haptene, enzyme) in the desired way substantially to the protective layer.

In FIG. 3 a cuvette 2 of the cuvette-set matrix and the corresponding source 10 of measurement beams together with the measurement beams 22 emitted from same are seen. The measurement beams 22 pass via the liquid 14 in the cuvette 2 through the optical window 16 of the cuvette to the corresponding detector 12 in the detector matrix 11. The matrix 9 of measurement beams is provided with limiters 13 for the protection of each cuvette from radiation disturbing the measurement. The sources of measurement beams are fitted above the cuvettes and the detectors below the cuvettes.

Further, it can be seen from FIG. 3 that the part 33 of the optical window 16 pervious to the beams of measurement may be made of a material totally different from the material of the other parts of the cuvette-set matrix. On the upper face of this part 33 pervious to the beams of measurement there may be a layer 34 that is made of the same material as the other parts of the cuvette-set matrix. In such a case, if the layer 34 is very thin, it does not prevent the passage of the beams of measurement 22 onto the detector 26 to a major extent. In some cases the layer 34 may function as the optical window alone. In the walls 2 the same material, as a thicker construction, prevents the passage of radiation from the adjoining cuvettes and any other external radiation almost completely.

If the material of the cuvette set matrix, in other respects except for the part 33, is not pervious to the beams of measurement, limiters 13 are unnecessary. The layer 34 shown in FIG. 3 can be extruded out of the same material as the cuvette-set matrix is made of, with the exception of part 33. In such a case, if the material is chosen so that the desired type of fixing of a certain reagent (e.g., antigen, antibody, haptene, or enzyme) to the material concerned is obtained, the layer 34 constitutes an additional face for the reagent. Either the part 33 or the layer 34 may also be used as a filter, e.g., for selecting the wave length of the measurement radiation. Of course, either the part 33 or the layer 34 may also be used in order to prevent the access of a certain type of radiation to the detector 12. Also, the part 33 may act so as to inhibit the access of a certain type of radiation to the detector 12, and the layer 34 may at the same time function as a filter for the transfer of a desired type of radiation to the detector 12.

The invention is not confined to the above embodiments alone, but it may show even considerable variation within the scope of the patent claims.

What is claimed is:

1. A set of cuvettes intended for use in a vertical measurement photometer, said cuvette set comprising a plurality of cuvettes wherein each cuvette comprises (a) side walls which are provided with a layer of material that prevents measurement radiation and/or light directed at said walls from passing through said walls, and (b) a bottom measurement window for optical reading, wherein said measurement window is coated with a layer of the same material which is contained in said side walls, said layer being sufficiently thin to allow the passage of a majority of said radiation through said window.

* * * * *